(12) United States Patent
Shi (10) Patent No.: US 10,779,853 B2
(45) Date of Patent: Sep. 22, 2020

(54) SHEATH TYPE DISPOSABLE SAFETY SCALPEL

(71) Applicant: STERILANCE MEDICAL (SUZHOU) INC., Suzhou, Jiangsu (CN)

(72) Inventor: Guoping Shi, Suzhou (CN)

(73) Assignee: STERILANCE MEDICAL (SUZHOU) INC., Jiangsu (CN)

( * ) Notice: Subject to any disclaimer, the term of this patent is extended or adjusted under 35 U.S.C. 154(b) by 0 days.

(21) Appl. No.: 16/332,930

(22) PCT Filed: Sep. 12, 2017

(86) PCT No.: PCT/CN2017/101381
§ 371 (c)(1),
(2) Date: Jul. 1, 2019

(87) PCT Pub. No.: WO2018/050048
PCT Pub. Date: Mar. 22, 2018

(65) Prior Publication Data
US 2019/0314049 A1    Oct. 17, 2019

(30) Foreign Application Priority Data
Sep. 13, 2016 (CN) .......................... 2016 1 0816550

(51) Int. Cl.
*A61B 17/3211* (2006.01)
*A61B 17/00* (2006.01)
(52) U.S. Cl.
CPC ... *A61B 17/3211* (2013.01); *A61B 2017/0023* (2013.01); *A61B 2017/32113* (2013.01)
(58) Field of Classification Search
CPC ........ A61B 17/3211; A61B 2017/0023; A61B 2017/32113
(Continued)

(56) References Cited

U.S. PATENT DOCUMENTS 5,417,704 A * 5/1995 Wonderley ......... A61B 17/3211
30/162
6,626,925 B2   9/2003 Newman et al.
(Continued)

FOREIGN PATENT DOCUMENTS

CN      2621611 Y    6/2004
CN    102871706 A    1/2013
(Continued)

OTHER PUBLICATIONS

Nov. 3, 2017 International Search Report issued in International Patent Application No. PCT/CN2017/101381.

*Primary Examiner* — Hwei-Siu C Payer
(74) *Attorney, Agent, or Firm* — Oliff PLC (57) ABSTRACT

A sheath type disposable safety scalpel consists of the blade, handle and sheath, and when the sheath slides forward and backward in relation to the handle, the blade shows the extension and retraction states in the sheath, wherein: the positioning mechanism consists of the button on the sheath and the blade protection locking notch and blade exposure locking notch on the handle, and the unlocking inclined surface is set under the blade protection locking notch and blade protection locking notch, and when the button is pressed and pulled, the locking head touches the unlocking inclined surface and climbs out of the locking notch along the unlocking inclined surface to unlock, so that sheath slides between blade protection locking notch and blade exposure locking notch in relation to the handle. The scalpel breaks the monopolization of traditional positioning mechanism, improves safety of scalpel and improves user hand feeling and sound experience.

10 Claims, 9 Drawing Sheets

(58) Field of Classification Search
USPC .......................................................... 30/151
See application file for complete search history.

(56) References Cited

U.S. PATENT DOCUMENTS

| | | | | |
|---|---|---|---|---|
| 7,087,067 | B2* | 8/2006 | Kehr ................. | A61B 17/3213 |
| | | | | 30/136.5 |
| 7,153,317 | B2* | 12/2006 | Kanodia ............ | A61B 17/3211 |
| | | | | 606/167 |
| 7,346,989 | B2* | 3/2008 | Shi .................... | A61B 17/3213 |
| | | | | 30/151 |
| 9,636,141 | B2* | 5/2017 | Shi .................... | A61B 17/3217 |
| 9,839,442 | B2* | 12/2017 | Shi .................... | A61B 17/3217 |
| 2005/0228420 | A1 | 10/2005 | Harding et al. | |
| 2019/0314049 | A1* | 10/2019 | Shi .................... | A61B 17/3211 |
| 2019/0365406 | A1* | 12/2019 | Milton .............. | A61B 17/3213 |

FOREIGN PATENT DOCUMENTS

| | | | |
|---|---|---|---|
| CN | 103976776 | A | 8/2014 |
| CN | 205215318 | U | 5/2016 |
| CN | 106236201 | A | 12/2016 |

* cited by examiner

SHEATH TYPE DISPOSABLE SAFETY SCALPEL

TECHNICAL FIELD

The present invention relates to the medical surgical scalpel, particularly to a disposable safety scalpel with blade shield (also known as a disposable safety scalpel).

BACKGROUND OF INVENTION

The disposable safety scalpel has been developed for decades and the improvement of the scalpels has been made several times and the current disposable safety scalpel is turning to be mature and the design idea for the product is upgraded as paying more attention to the user experience on the premise of ensuring the safety. Such as hand feel, visual feel and user psychology, etc.

The prior art which is close to the present invention is U.S. Pat. No. 6,626,925B2 with the title of safety surgical scalpel. The scalpel of present invention consists of a blade, a handle and a sheath and the sheath is set with a button and a locking head, and the handle is set with a sliding channel, which is set with a blade protection locking notch at the front end and set with a blade exposure locking notch at the rear end, and when the button is pressed and pushed, the button drives the locking head to make the sheath slide between the blade protection locking notch and blade exposure locking notch and finally makes the blade extend and retract relative to the front end of sheath.

The sliding mechanism and positioning mechanism formed by the matching of locking head, sliding channel, blade protection locking notch and blade exposure locking notch are typical in the product structure design of the disposable safety scalpel. The feature of this structure type is: the structure is simple and reliable; the design is reasonable and it's easy to be manufactured. And it's typical in the scalpel field in recent 10 years and it's hard to be surpassed. However, some shortcomings were exposed during the long-term use, for example the button is the cantilever beam structure and the sheath is opened to expose the blade tip when it's pressed lightly, so the sense of safety is not high. And from the clinic use, the user experience of this structure is required to be improved.

Therefore, the present invention proposes the new challenges for the traditional structure of disposable safety scalpel from the creativity and breakthrough aspect and it's aimed to design a new sliding and positioning mechanism suitable for the disposable safety scalpel to break the traditional monopolization and overcome the defects of prior art.

DISCLOSURE OF THE INVENTION

The present invention provides a sheath type disposable safety scalpel with the aim to break the traditional design monopolization of positioning mechanism for the scalpel sheath and handle and design a new positioning mechanism suitable for the scalpel and solve the problem of safety and bad user experience in the prior art.

In order to achieve the above purpose, the present invention applies the technical plan: a sheath type disposable safety scalpel consists of a blade, a handle and a sheath and the blade is fixed on the front end of handle and the sheath covers the front end of handle and is connected with the handle through a sliding mechanism and a positioning mechanism.

Wherein: the positioning mechanism is formed by the matching of a button set on the top of sheath and a blade protection locking notch and a blade exposure locking notch at the side of the handle.

The button is a flexible arm extending from the sheath and the flexible arm is set with a pressing portion, the flexible arm is transformed flexibly in the width direction of the handle when pressing the button, and a locking head is set at the end of flexible arm facing the side of handle.

The blade protection locking notch is located in the blade protection position at the lateral face at the front of handle and the blade exposure locking notch is located in the blade exposure position at the lateral face in the middle of handle; the blade protection locking notch is the first concave notch, and a first blocking face is set at the right side of the first concave notch from the front face of the blade protection locking notch, and a first unlocking inclined face is set at the lower portion of first concave notch; the blade exposure locking notch is the second concave notch, and a second blocking face is set at the left side of the second concave notch, and a second unlocking inclined face is set at the lower portion of the second concave notch.

Under the assembly state and when the sheath presents the blade protection state in relation to the handle, the locking head is inserted into the blade protection locking notch to form the positioning and locking of blade protection and when the sheath presents the blade exposure state in relation to the handle, the locking head is inserted into the blade exposure locking notch to form the positioning and locking of blade exposure; under the blade protection state, when the button is pressed and pulled backward, the locking head climbs out of the blade protection locking notch along the first unlocking inclined face to unlock and slides backward along with the sheath until it drops in the blade exposure locking notch; under the blade exposure state, when the button is pressed and pushed forward, the locking head climbs out of the blade exposure locking notch along the second unlocking inclined face to unlock and slides forward along with the sheath until it drops in the blade protection locking notch, so that sheath slides between blade protection locking notch and blade exposure locking notch in relation to the handle.

The above described technical solution is explained as follows.

1. In above described technical solution, the "front" in said "front portion" and "front end" means the direction in which the blade tip point to with respect to the scalpel in the present invention. The "rear" in said "rear end" means the direction opposite to the "front".

2. In above described technical solution, the "front face" means the lateral face which could be seen when the blade tip faces left and the button faces up with respect to the scalpel in the present invention. "Reverse face" means the face opposite to the front face. The thickness direction of scalpel is from front face to reverse face. The length direction is from front to back of scalpel. The width direction of scalpel is from top to bottom under front face or reverse face state. The figures of complete scalpel in the present invention are the gestures of scalpel held by the right hand with the thumb acting on the button.

3. In above described technical solution, "top" means the top of scalpel when it's held by the right hand. Said "lateral face" means the front face or reverse face of scalpel. Said "width direction" means the top and bottom direction when it's held by the right hand and the thickness direction means the front and back direction when it's held by the right hand.

4. In above described technical solution, said "concave notch" means recess on the handle. Said "inclined surface" has three types: the first type is plane type inclined surface; the second type is the concave type inclined surface, i.e. the inclined surface consists of many straight lines in the inclined direction to form the concave or convex in the straight inclined direction, but it's essentially the inclined surface; the third type is the cambered type inclined surface, i.e. it consists of at least one concave arc or/and convex arc in the inclined surface, but it's essentially the inclined surface. In the present invention, any type is applicable and it could be determined according to the practical situation.

5. In above described solution, the said "positioning locking" means the temporary locking state of sheath with respect to handle and the locking state could be released by pressing the button. The "positioning locking" is different from "deadlocking state". The deadlocking state means state of permanently locking sheath with respect to handle. It's the permanent locking state and the deadlocking state could only be released by damage.

6. In above described technical solution, said "sliding mechanism" consists of the outer edge at front of handle and inner edge of sheath, and the handle is set with the protruding rib along the length direction in the front face and rear face and the sheath inner edge is set with the recess in relation to the protruding rib and the protruding rib and recess combines to form the sliding guiding mechanism. "Sliding mechanism" is the prior art.

The design principle and idea of present invention is: the present invention relates to the disposable safety scalpel with blade shield. In order to improve the safety of scalpel, improve the user hand feeling, break the monopolization of traditional positioning mechanism, the present invention sets the unlocking inclined surface under the blade protection locking notch and blade exposure locking notch. When the button is pressed and pulled, the locking head touches the unlocking inclined surface and climbs out of the locking notch along the unlocking inclined surface to unlock, so that sheath slides between blade protection locking notch and blade exposure locking notch in relation to the handle.

Figure 21:
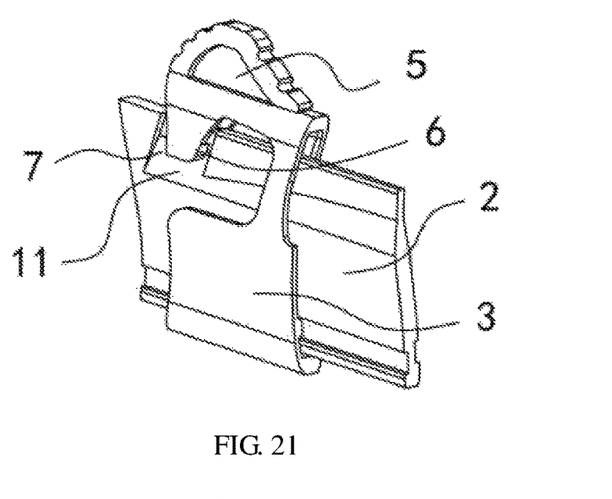
FIG. 21 is the schematic diagram of positioning mechanism of the embodiment of present invention.

Due to the application of the above described technical solution, the present invention has the following advantages and effect in comparison with the prior art:

1. Although the traditional positioning mechanism consists of the locking head and the blade protection locking notch and blade exposure locking notch, the unlocking principles are quite different. The unlocking principle of traditional positioning mechanism is to set the lateral outlet under the blade protection locking notch and blade exposure locking notch (see FIG. 23) and when the locking head is in the locking notch, it uses the flexible deformation of button to move the locking head from locking position to the outlet, and then uses the drawing force to force the locking head into the transversal sliding channel (L type sliding channel 23) and move along the transversal sliding channel. But the unlocking principle of the positioning mechanism in the present invention is to set the unlocking inclined surface under the blade protection locking notch and blade exposure locking notch (see FIGS. 21 and 22) and when the button is pressed and drawn, it uses the locking head connection unlocking inclined surface and climbs out of the locking notch along the unlocking inclined surface for unlocking. During unlocking of traditional positioning mechanism, the locking head moves out along the lateral outlet and the flexible arm doesn't bear the pressure in the thickness direction. But during the unlocking of positioning mechanism in the present invention, the locking head climbs out of the locking notch along the unlocking inclined surface, and the flexible arm bears the pressure from the unlocking inclined surface in the thickness direction. In addition, during the unlocking of traditional positioning mechanism, the locking head moves out from the radial direction of locking notch, but during the unlocking of positioning mechanism in the present invention, the locking head climbs out from the axial direction of locking notch. Therefore, the principles of two types are completely different. From the design of the positioning mechanism of scalpel in this field, the present invention breaks the traditional design monopolization of the positioning mechanism of sheath and handle and has the material characteristics and obvious improvement.

2. Although the traditional positioning mechanism not only requires the cooperation of locking head and blade protection locking notch and blade exposure locking notch, but also sets the transversal sliding channel between the blade protection locking notch and blade exposure locking notch and the locking head must be connected with the blade protection locking notch and blade exposure locking notch through the transversal sliding channel. The present invention gets rid of the restriction of transversal sliding channel and is not limited by the transversal sliding channel.

3. The locking head in the present invention climbs out of the locking notch along the unlocking inclined surface and the flexible arm bears the pressure from the unlocking inclined surface from the handle thickness direction during the climbing process, so the pressure to press the button during the unlocking is heavier than the traditional positioning mechanism, i.e. the pressure of unlocking in the present invention is heavier than that in the traditional positioning mechanism, that is to say, the locking of the positioning mechanism in the present invention is more reliable and safer than that of the traditional positioning mechanism and it's not prone to cause the sheath unlocking due to misoperation and accidental touch.

4. During the unlocking process of locking head of present invention, the pressing force on the button is gradually increased along the climbing of locking head from the unlocking inclined surface and it suddenly starts with the temporary friction sound when it climbs out of the locking notch and it provides the better hand feeling and sound experience in comparison with the traditional positioning mechanism.

5. If the concave cambered surface is designed between the blade protection locking notch and blade exposure locking notch on the handle, i.e. the concave direction of concave cambered surface makes the handle thickness between the blade protection locking notch and blade exposure locking notch show the state of "thin in the middle and thick at the ends". When the sheath slides between the blade protection locking notch and blade exposure locking notch, the user feels light in the middle section and feels heavier at the ends, and when it drops in the blade protection locking notch and blade exposure locking notch, it will sound "Dee", so it has better hand feeling and sound experience in comparison with the traditional positioning mechanism.

The number description of above described drawings is as follows:

1. Blade; 2. Handle; 3. Sheath; 4. Front opening; 5. Button; 6. Locking head; 7. Blade protection locking notch; 8. Blade exposure locking notch; 9. Pressing position; 10. First blocking face; 11. First unlocking inclined face; 12. Second blocking face; 13. Second unlocking inclined face; 14. Transition inclined face; 15. Concave cambered surface; 16. Lock notch; 17. Third blocking face; 18. Cambered surface; 19, Assembly inclined surface; 20 Protruding rib; 21 Recess; 22. Cambered step face; 23, L type sliding channel.

SPECIFIC EMBODIMENT

With reference to the accompanying drawings and embodiment, the present invention will be described in detail.

Embodiment: A Sheath Type Disposable Safety Scalpel

As shown in FIG. 1-4, the sheath type disposable safety scalpel consists of a blade 1, a handle 2 and a sheath 3 and the blade 1 is fixed on the front end of handle 2 and the sheath 3 covers the front end of handle 2 and is connected with the handle 2 through a sliding mechanism and a positioning mechanism.

The said sliding mechanism consists of the outer edge at front of handle 2 and inner edge of sheath 3, and the handle 2 is set with the recess 21 along the length direction in the front face and rear face (see FIG. 12-16) and the sheath 3 inner edge is set with the protruding rib 20 (see FIG. 7-8 and FIG. 15-16) in relation to the recess 21 and the protruding rib 20 and recess 21 combines to form the sliding guiding mechanism.

The positioning mechanism is formed by the matching of a button 5 (see FIG. 1-4) set on the top of sheath 3 and a blade protection locking notch 7 (see FIGS. 9 and 12) and a blade exposure locking notch 8 (see FIGS. 9 and 12) at the side of the handle 2.

The button 5 is a flexible arm extending from the sheath 3 (see FIGS. 5 and 6) and the flexible arm is set with a pressing portion 9 (see FIGS. 5 and 6) and the flexible arm of pressing button 5 is transformed flexibly in the width direction of the handle 2, and a locking head 6 is set at the end of flexible arm facing the side of handle 2 (see FIG. 5-8). The locking head 6 is the convex or lug structure perpendicular to the lateral face of handle 2 (see FIGS. 7 and 15).

Figure 1:
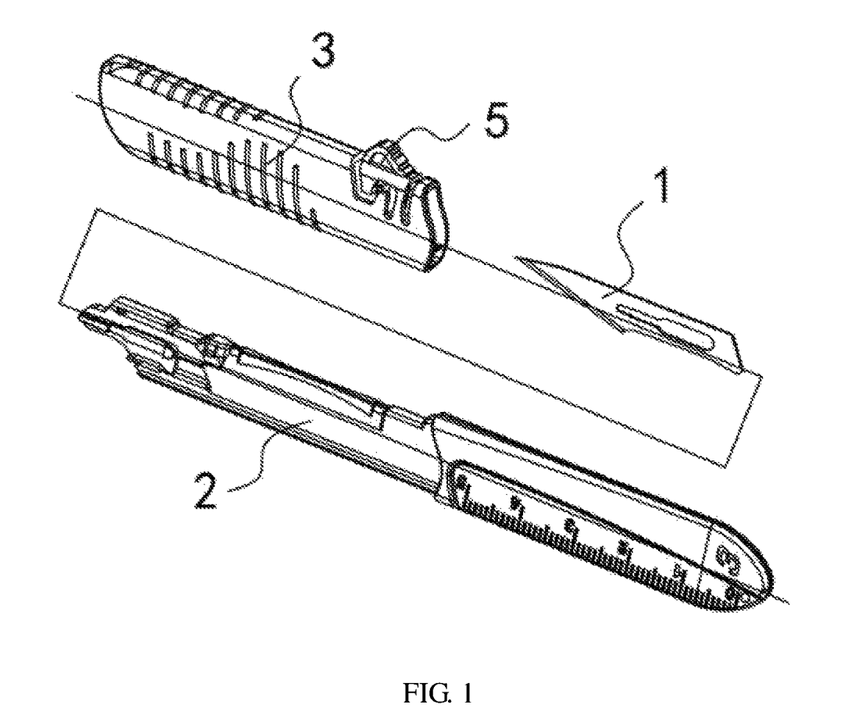
FIG. 1 is the exploded perspective view of disposable safety scalpel of embodiment of present invention (I)
Figure 2:
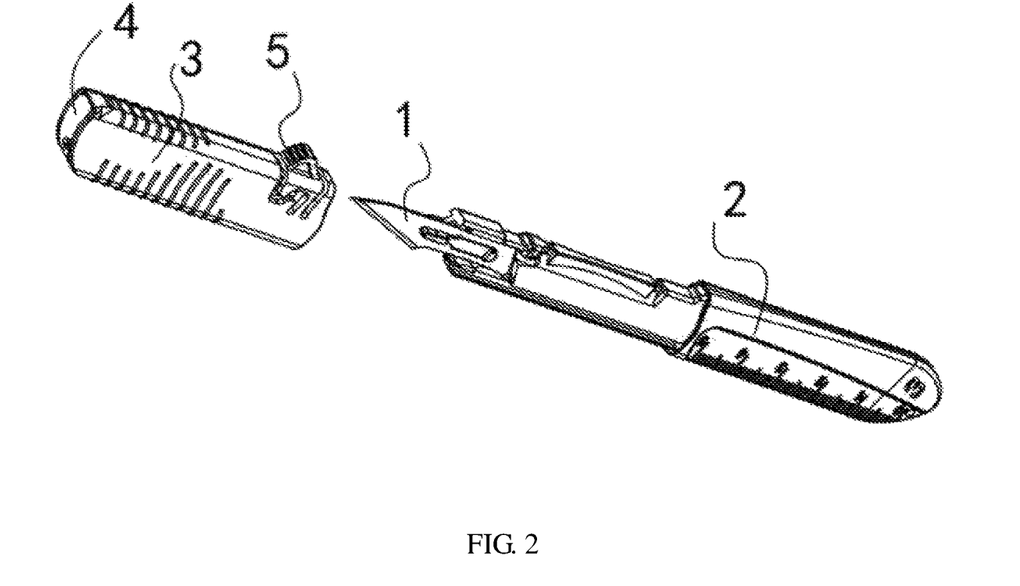
FIG. 2 is the exploded perspective view of disposable safety scalpel of embodiment of present invention (II)
Figure 3:
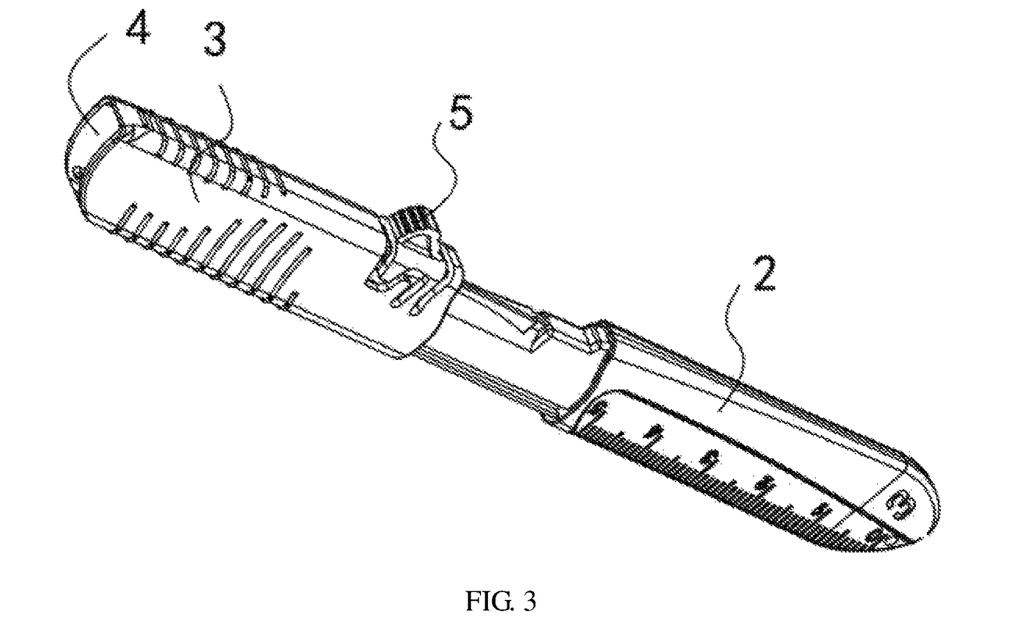
FIG. 3 is the perspective view of disposable safety scalpel of embodiment of present invention in the blade protection state.
Figure 4:
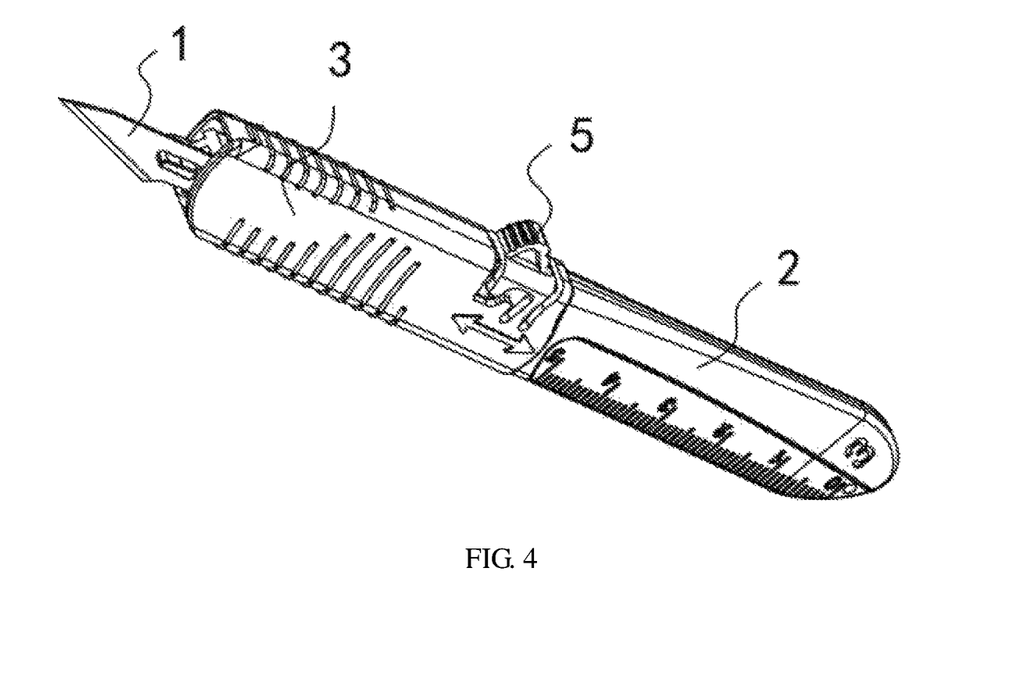
FIG. 4 is the perspective view of disposable safety scalpel of embodiment of present invention in the blade exposure state.
Figure 5:
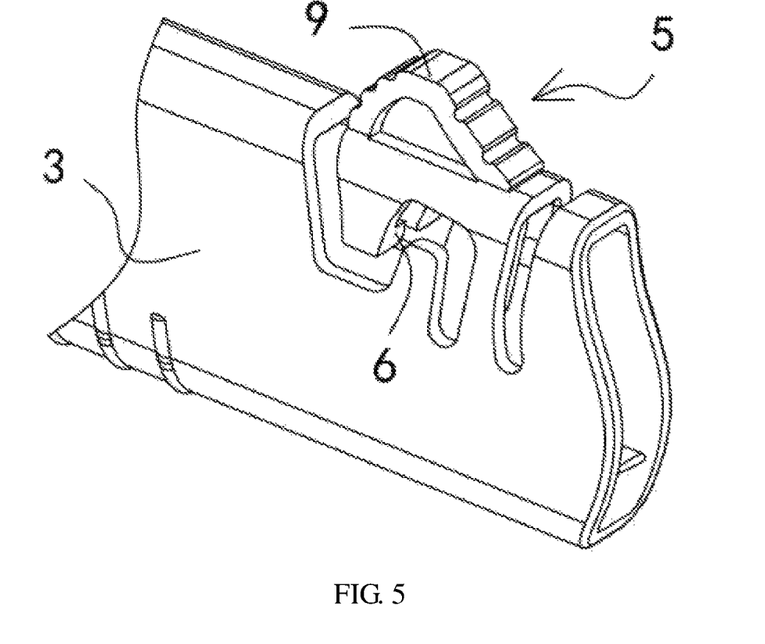
FIG. 5 is the perspective view of button on the sheath of present invention.
Figure 6:
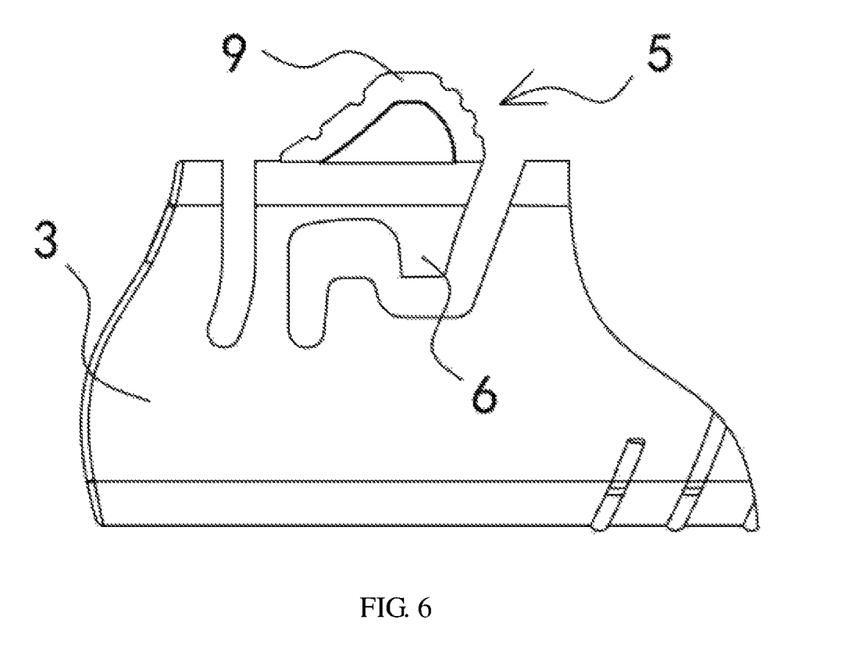
FIG. 6 is the front view of button on the sheath of present invention.
Figure 7:
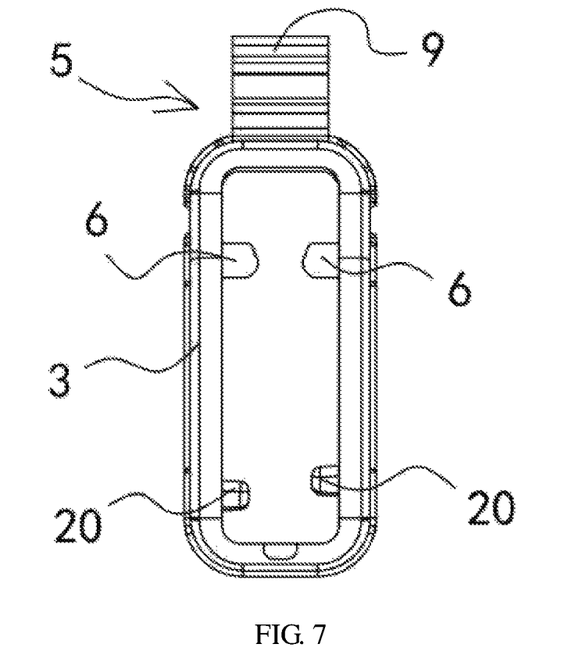
FIG. 7 is the side view of sheath of embodiment of present invention.
Figure 8:
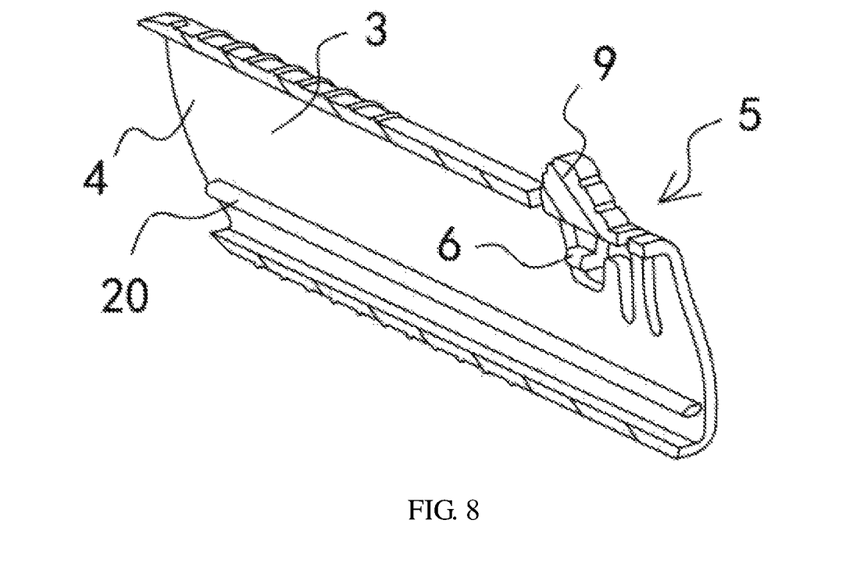
FIG. 8 is exploded cross sectional view of sheath of embodiment of present invention.
Figure 9:
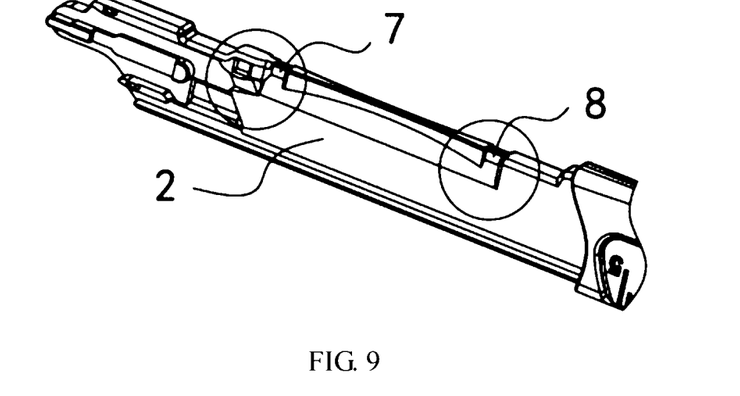
FIG. 9 is the perspective view of front of handle of embodiment of present invention.

The blade protection locking notch 7 is located in the blade protection position at the lateral face at the front of handle 2 and the blade exposure locking notch 8 is located in the blade exposure position at the lateral face in the middle of handle 2 (see FIG. 9). The blade protection locking notch 7 is the first concave notch (see FIG. 10) and a first blocking face 10 is set at the left and right side of the first concave notch from the front face of the blade protection locking notch 7 and a first unlocking inclined face 11 is set at the lower portion of first concave notch (see FIG. 10). The blade exposure locking notch 8 is the second concave notch (see FIG. 11) and a second blocking face 12 is set at the left and right side of the second concave notch and a second unlocking inclined face 13 is set at the lower portion of second concave notch (see FIG. 11).

Under the assembly state and when the sheath 3 presents the blade protection state in relation to the handle 2 (see FIG. 3), the locking head 6 is inserted into the blade protection locking notch 7 to form the positioning and locking of blade protection (see FIG. 15) and when the sheath 3 presents the blade exposure state in relation to the handle 2, the locking head 6 is inserted into the blade exposure locking notch to form the positioning and locking of blade exposure. Under the blade protection state, when the button 5 is pressed and pulled backward, the locking head 6 climbs out of the blade protection locking notch 7 along the first unlocking inclined face 11 to unlock (see FIG. 16) and slides backward along the sheath 3 until it drops in the blade exposure locking notch 8; Under the blade exposure state, when the button 5 is pressed and pushed forward, the locking head 6 climbs out of the blade exposure locking notch 8 along the second unlocking inclined face 13 to unlock and slides forward along the sheath until it drops in the blade protection locking notch 7, so that sheath 3 slides between blade protection locking notch 7 and blade exposure locking notch 8 in relation to the handle 2.

In this embodiment, the said first unlocking inclined face 11 is set just below the blade protection locking notch 7 (see FIG. 12) and when the button 5 is pressed, the slant of first unlocking inclined face 11 makes the locking head 6 climb out of the blade protection locking notch 7 from below the first concave notch (see FIG. 16). The said second unlocking inclined face 13 is set just below the blade exposure locking notch 8 (see FIG. 12-13) and when the button 5 is pressed, the slant of second unlocking inclined face 13 makes the locking head 6 climb out of the blade exposure locking notch 8 from below the second concave notch. The first unlocking inclined face 11 and the second unlocking inclined face 13 are connected by the transition inclined face 14 (see FIG. 12-13). The concave cambered surface 15 is connected between the blade protection locking notch 7 and blade exposure locking notch 8 on the handle 2 (see FIG. 12-13), i.e. the concave direction of concave cambered surface 15 makes the handle 2 thickness show the state of "thin in the middle and thick at the ends". When the sheath 3 slides between the blade protection locking notch 7 and blade exposure locking notch 8, the user feels light in the middle section and feels heavier at the ends, and when it drops in the blade protection locking notch 7 and blade exposure locking notch 8, it will sound "Dee", so it has better hand feeling and sound experience in comparison with the traditional positioning mechanism.

Figure 15:
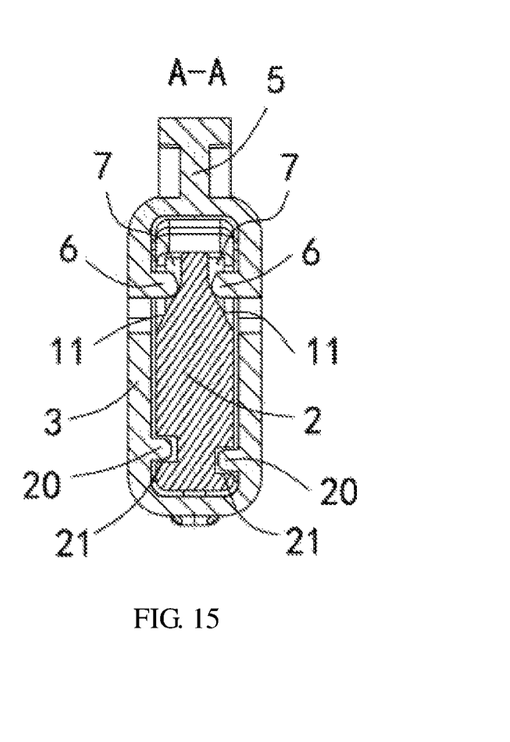
FIG. 15 is A-A cross sectional view of button when the button is not pressed in FIG. 14.
Figure 16:
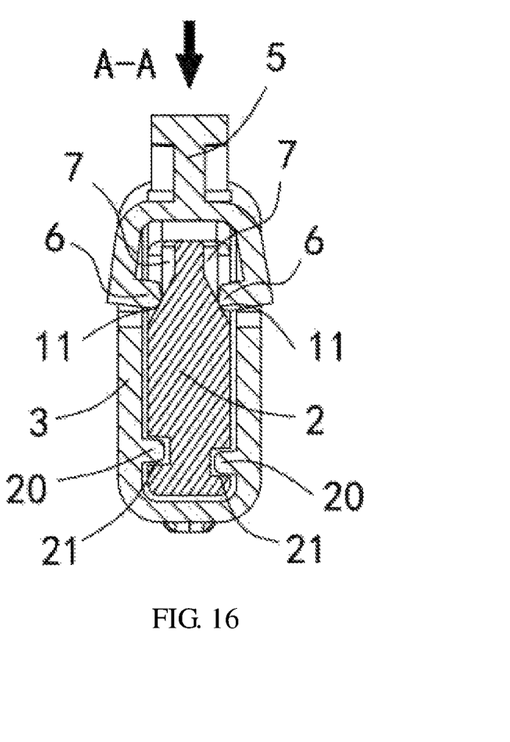
FIG. 16 is A-A cross sectional view of button when the button is pressed in FIG. 14.

In this embodiment, the said blade protection locking notch 7 and blade exposure locking notch 8 are set at the front side and back side of the handle 2 and the two locking heads 6 are set on the button 5 in relation to the blade protection locking notch 7 and blade exposure locking notch 8, with one locking head 6 for the front face and one locking head 6 for the back face (see FIG. 15-16).

Figure 17:
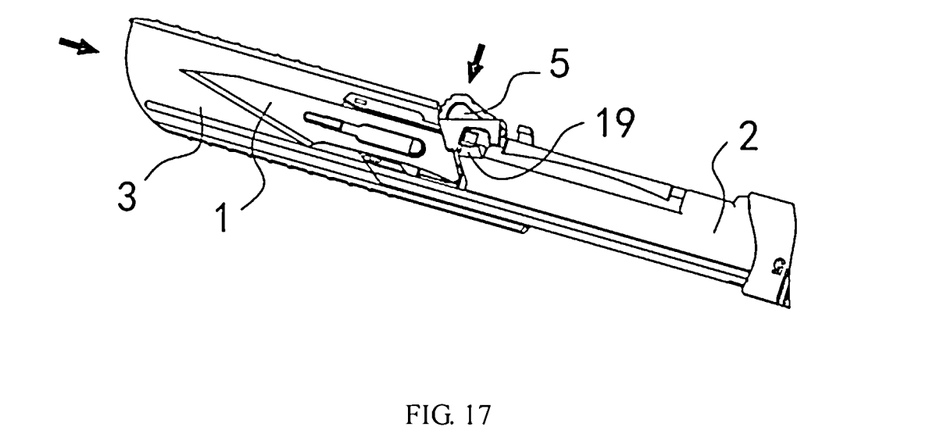
FIG. 17 is the view of sheath installation of embodiment of present invention.

In this embodiment, in order to improve the safety, the blade protection locking notch 7 is set with a lock notch 16 (see FIG. 10), which is a third concave notch and a third blocking face 17 are set at the left, right and lower position from the front face of lock notch 16 (see FIG. 10), and a cambered surface 18 (see FIG. 10) or slope is set between the lock notch 16 and blade protection locking notch 7 and the cambered surface 18 or slope could make the locking head 6 slide from blade protection locking notch 17 into the lock notch 16 under the forward driving force. For the convenience of installing the sheath 3, an assembly inclined surface 19 is set under the lock notch 16 (see FIG. 10) and the assembly inclined surface 19 is connected with or adjacent to the first unlocking inclined face 11 on the rear end and it leads to the installation base direction of the blade 1 on the front end, and when the sheath 3 covers the handle 2, press the button 5 and push the sheath 3 backward, then the locking head 6 slides from the assembly inclined surface 19 to the blade protection locking notch 7 to lock the blade protection (see FIG. 17).

The operation procedure of embodiment s described as follows

Firstly, the initial state before using the scalpel

Figure 18:
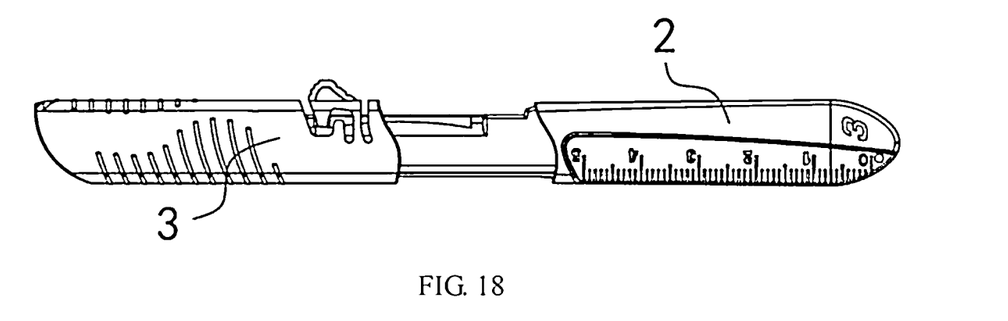
FIG. 18 is the view of disposable safety scalpel of embodiment of present invention in the blade protection state.

FIG. 18 is such state. From the FIG. 18, it's known that the locking head 6 is inserted into the blade protection locking notch 7 and it makes the sheath 3 in the positioning and locking state of blade protection in relation to the handle 2. Under the blade protection state, if the sheath 3 is to be opened, the button 5 is pressed and pulled backward, and the locking head 6 climbs out of the blade protection locking notch 7 along the first unlocking inclined face 11 to unlock and slides backward along the sheath 3 until it drops in the blade exposure locking notch 8 to enter the blade exposure state.

Secondly, the operation state of scalpel

Figure 19:
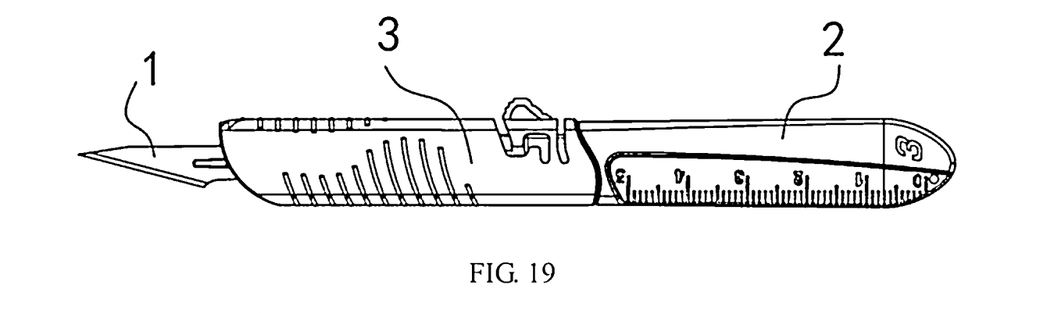
FIG. 19 is the view of disposable safety scalpel of embodiment of present invention in the blade exposure state.

FIG. 19 is such state. From the FIG. 19, it's known that the locking head 6 is inserted into the blade exposure locking notch 8 and it makes the sheath 3 in the positioning and locking state of blade exposure in relation to the handle 2 and the blade 1 extends from the front opening of sheath 3 to be in the operation state.

Thirdly, the closing state after use of scalpel

FIG. 18 is such state. After the use, press the button 5 and push forward the button 5 to make the sheath 3 slide forward to the front end in relation to the handle 2. From the FIG. 18, it's known that the locking head 6 is inserted into the blade protection locking notch 7 and it makes the sheath 3 in the positioning and locking state of blade protection in relation to the handle 2.

Fourthly, enter deadlocking state after use of scalpel.

Figure 20:
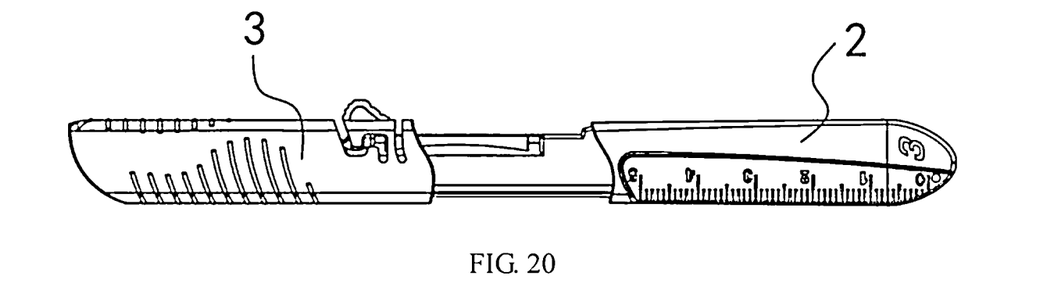
FIG. 20 is the view of disposable safety scalpel of embodiment of present invention in the deadlocking state.

FIG. 20 is such state. This state is transited from the above closing state as follows: under the blade protection state, press and push forward the button 5 to make the locking head 6 slide from cambered surface 18 into lock notch 16 to enter the deadlocking state and it could not be reused.

The following the description about the other embodiments and changes of the present invention:

1. In the above embodiment, the said blade protection locking notch 7 and blade exposure locking notch 8 are set at the front side and back side of the handle 2, i.e. the blade protection locking notch 7 and blade exposure locking notch 8 are set at two sides of the handle 2. The present invention is not limited to this, the blade protection locking notch 7 and blade exposure locking notch 8 could be set at one side of the handle 2, i.e. set at front side or back side. The quantity of the corresponding locking head 6 could be changed.

Figure 22:
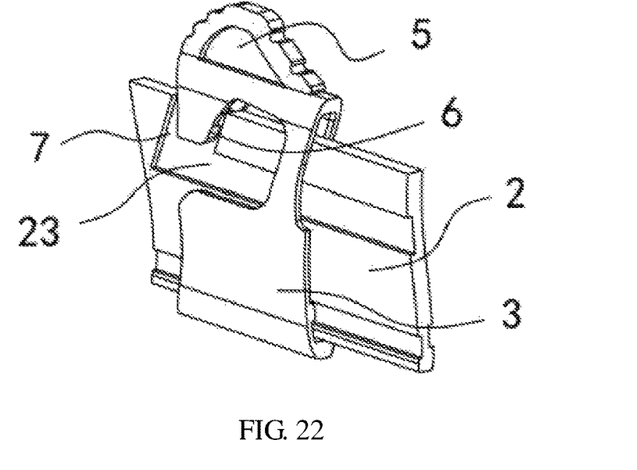
FIG. 22 is the schematic diagram of positioning mechanism of another embodiment of present invention.
Figure 23:
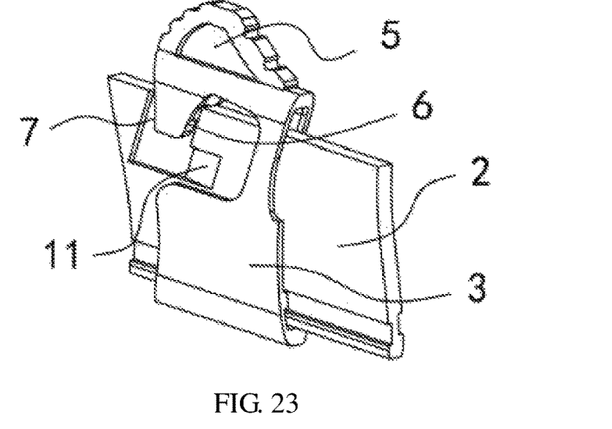
FIG. 23 is the schematic diagram of traditional positioning mechanism.

2. In above embodiment, the first unlocking inclined face 11 is set just below the blade protection locking notch 7 (see FIG. 21) and second unlocking inclined face 13 is set just below the blade exposure locking notch 8 (see FIG. 12-13) The present invention is not limited to this and could be changed as follows:

(1) To set the first unlocking inclined face 11 at lower right side of the blade protection locking notch 7 (see FIG. 22). When the button 5 is pressed, the locking head 6 moves to the bottom of blade protection locking notch 7, and when the button 5 is pulled backward, the slant of first unlocking inclined face 11 makes the locking head 6 climb out of the blade protection locking notch 7 from below the first concave notch. To set the second unlocking inclined face 13 at lower left side of the blade exposure locking notch 8. When the button 5 is pressed, the locking head 6 moves to the bottom of blade exposure locking notch 8, and when the button 5 is pushed forward, the slant of second unlocking inclined face 13 makes the locking head 6 climb out of the blade exposure locking notch 8 from below the second concave notch.

(2) To set the first unlocking inclined face 11 just below the blade protection locking notch 7 and set the second unlocking inclined face 13 at lower left side of the blade exposure locking notch 8.

(3) To set the first unlocking inclined face 11 at lower right side of the blade protection locking notch 7 and set the second unlocking inclined face 13 just below the blade exposure locking notch 8.

3. In the above embodiment, the first unlocking inclined face 11 and the second unlocking inclined face 13 are connected by the transition inclined face 14 (see FIG. 12-13). But the present invention is not limited to this, it's possible to not set the transition inclined face 14, but change it to the plane surface or curved surface.

Figure 12:
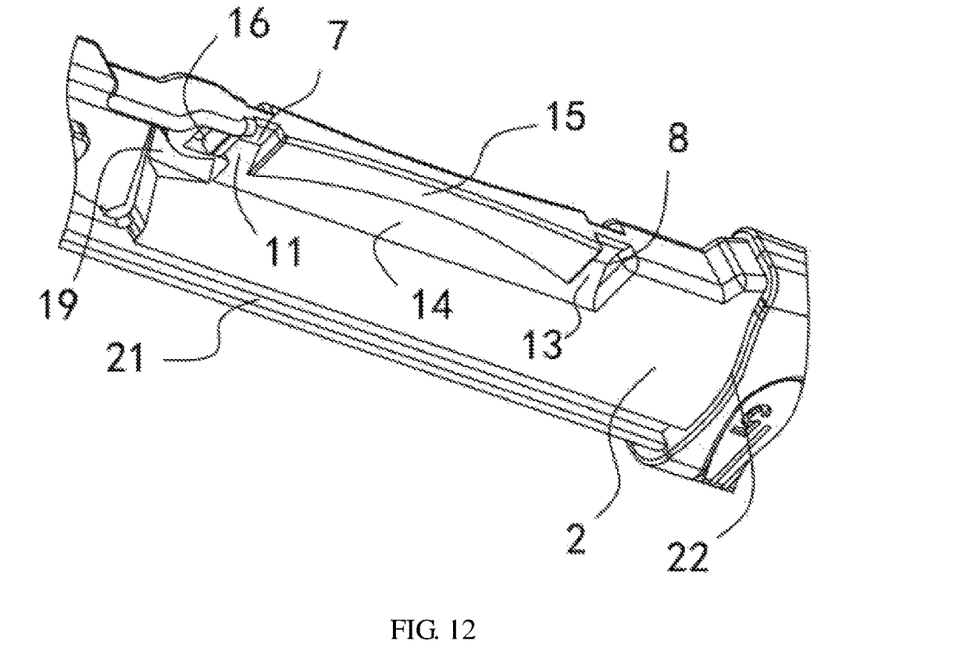
FIG. 12 is the local enlarged view of handle in the embodiment 1 of present invention.
Figure 13:
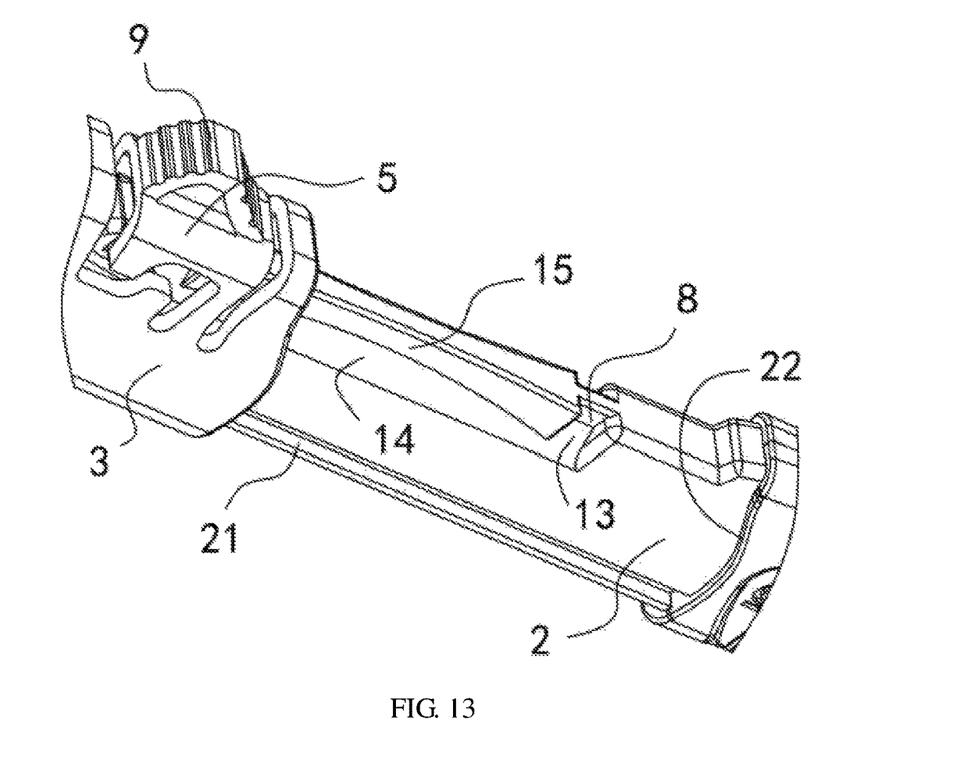
FIG. 13 is the local enlarged view of assembly of sheath and handle in the blade protection state in the embodiment of present invention.
Figure 14:
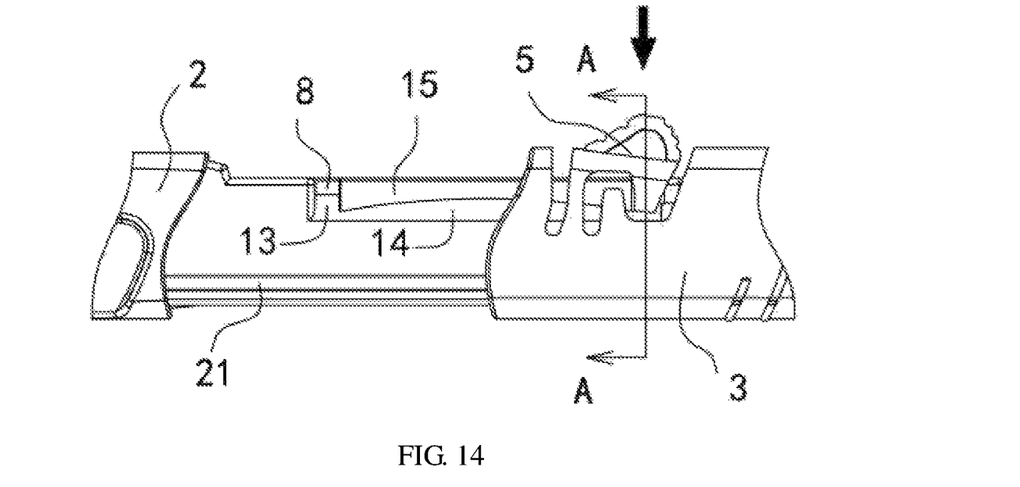
FIG. 14 is the local front view of assembly of sheath and handle in the blade protection state in the embodiment of present invention.

4. From the above embodiment, the blade protection locking notch 7 and blade exposure locking notch 8 on the handle 2 are connected by the concave cambered surface 15

(see FIG. 12-13). But the present invention is not limited to this, and it's possible to not set the concave cambered surface 15, but change it to the plane surface. If the concave cambered surface 15 is set, it could be thin in the middle and thick at the ends, or thick at one end and thin in the middle and at the other end. It could be determined according to the practical situation.

5. In the above embodiment, the locking head 6 is the convex or lug structure perpendicular to the lateral face of handle 2 (see FIGS. 7 and 15). The present invention is not limited to this, and the locking head 6 could be designed to be the convex or lug structure parallel to the lateral face of handle 2.

6. In the above embodiment, the button 5 is a flexible arm extending from the sheath 3. There are usually two types: the first type is the compact structure of button 5 and sheath 3 and the second type is the separate structure of button 5 and sheath 3 and they're connected through the insertion or assembly. The above embodiment is the first type (see FIG. 5-6).

Figure 10:
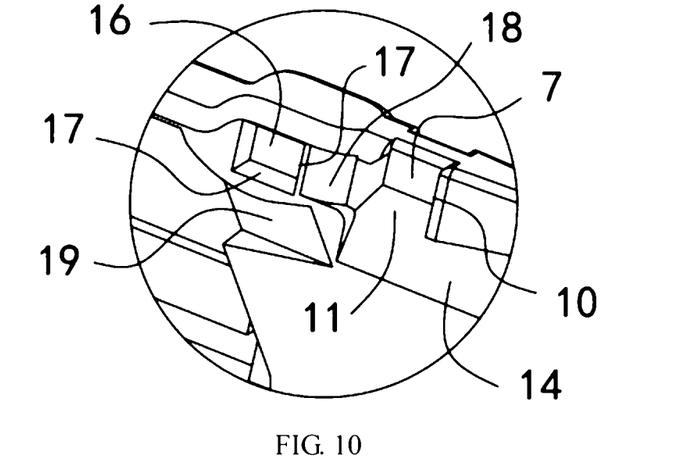
FIG. 10 is the local enlarged view of blade protection locking notch, lock notch and assembly inclined surface.

7, In the above embodiment, a first blocking face 10 is set at the left and right side of the first concave notch from the front face of the blade protection locking notch 7 (see FIG. 10). Actually, for the blade protection locking notch 7 in the present invention, it's necessary to set the first blocking face 10 at the right side of first concave notch and it's unnecessary to set the first blocking face 10 at the left side and it could be replaced by the other structure on the sheath 3 and handle 2, for example, it's possible to set a long channel on the sheath 3 and set the convex on the handle 2 corresponding to the long channel, so the combination of convex and long channel could limit the position at the left side of first blocking face.

Figure 11:
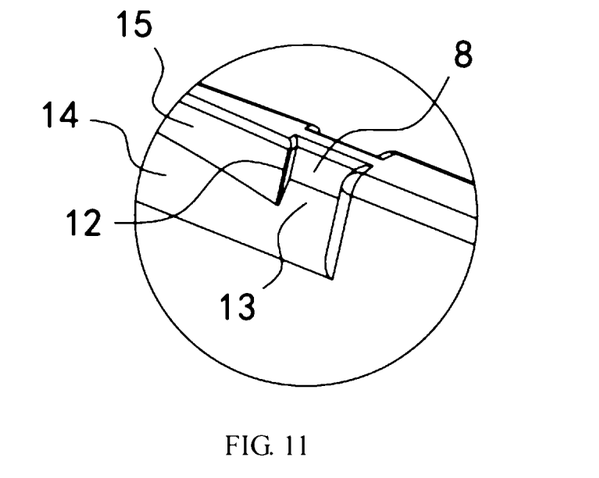
FIG. 11 is a local enlarged view of blade exposure locking notch in FIG. 9.

In a similar way, a second blocking face 12 is set at the left and right side of the second concave notch from the front face of the blade exposure locking notch 8 (see FIG. 11). Actually, for the blade exposure locking notch 8 in the present invention, it's necessary to set the second blocking face 12 at the left side of second concave notch and it's unnecessary to set the second blocking face 12 at the right side and it could be replaced by the other structure on the sheath 3 and handle 2, for example, it's possible to set a cambered step face 22 in the middle of handle (see FIG. 12-13), so when the sheath 3 slides backward, the rear end face of sheath 3 touches the cambered step face 22 to limit the position.

It should be noted that the above described embodiments are only for illustration of technical concept and characteristics of present invention with purpose of making those skilled in the art understand the present invention, and thus these embodiments shall not limit the protection range of present invention. The equivalent changes or modifications according to spiritual essence of present invention shall fall in the protection scope of present invention.

The invention claimed is:
1. A sheath type disposable safety scalpel, comprising:
a blade;
a handle; and
a sheath,
wherein:
the blade is fixed a front end of the handle, and the sheath covers the front end of the handle and is connected with the handle through a sliding mechanism and a positioning mechanism;
the positioning mechanism is formed by the matching of a button provided on a top of the sheath and a blade protection locking notch and a blade exposure locking notch at one side of the handle;
the button is a flexible arm extending from the sheath and the flexible arm is provided with a pressing portion, the flexible arm is transformed flexibly in a width direction of the handle when pressing the button, and a locking head is provided at the end of the flexible arm facing the side of the handle;
the blade protection locking notch is located in a blade protection position at a lateral face at a front of the handle, and the blade exposure locking notch is located in a blade exposure position at a lateral face in a middle of the handle;
the blade protection locking notch is a first concave notch, and a first blocking face is provided at a right side of the first concave notch from a front face of the blade protection locking notch, and a first unlocking inclined face is provided at a lower portion of the first concave notch;
the blade exposure locking notch is a second concave notch, and a second blocking face is provided at a left side of the second concave notch, and a second unlocking inclined face is provided at a lower portion of the second concave notch;
under the assembly state, when the sheath presents a blade protection state in relation to the handle, the locking head is inserted into the blade protection locking notch to form a positioning and locking of blade protection and when the sheath presents a blade exposure state in relation to the handle, the locking head is inserted into the blade exposure locking notch to form a positioning and locking of blade exposure;
under the blade protection state, when the button is pressed and pulled backward, the locking head climbs out of the blade protection locking notch along the first unlocking inclined face to unlock and slides backward along with the sheath until the locking head drops in the blade exposure locking notch;
under the blade exposure state, when the button is pressed and pushed forward, the locking head climbs out of the blade exposure locking notch along the second unlocking inclined face to unlock and slides forward along with the sheath until the locking head drops in the blade protection locking notch, so that the sheath slides between the blade protection locking notch and the blade exposure locking notch in relation to the handle.

2. The sheath type disposable safety scalpel according to claim 1 wherein the locking head is a convex or lug structure perpendicular to a lateral face of the handle.

3. The sheath type disposable safety scalpel according to claim 1 wherein the locking head is a convex or lug structure parallel to a lateral face of the handle.

4. The sheath type disposable safety scalpel according to claim 1 wherein the first unlocking inclined face is provided below the blade protection locking notch, when the button is pressed, a slant of the first unlocking inclined face makes the locking head climb out of the blade protection locking notch from below the first concave notch; the second unlocking inclined face is provided below the blade exposure locking notch, and when the button is pressed, a slant of the second unlocking inclined face makes the locking head climb out of the blade exposure locking notch from below the second concave notch.

5. The sheath type disposable safety scalpel according to claim 4 wherein the first unlocking inclined face and the second unlocking inclined face are connected by a transition inclined face.

6. The sheath type disposable safety scalpel according to claim 1 wherein the first unlocking inclined face is provided at a lower right side of the blade protection locking notch, and when the button is pressed, the locking head moves to a lower position of the blade protection locking notch, and when the button is pulled backward, a slant of the first unlocking inclined face makes the locking head climb out of the blade protection locking notch from a lower right side of the first concave notch; the second unlocking inclined face is provided at a lower left side of the blade exposure locking notch, and when the button is pressed, the locking head moves to a lower position of the blade exposure locking notch, and when the button is pushed forward, a slant of the second unlocking inclined face makes the locking head climb out of the blade exposure locking notch from a lower left side of the second concave notch.

7. The sheath type disposable safety scalpel according to claim 1 wherein the blade protection locking notch and the blade exposure locking notch are provided at a front side and/or a back side of the handle and the locking head is provided on the button according to the quantity and position of the blade protection locking notch and the blade exposure locking notch.

8. The sheath type disposable safety scalpel according to claim 1 wherein the blade protection locking notch and the blade exposure locking notch on the handle are connected by a concave cambered surface, and a concave shape makes the handle thin in the middle and thick at the ends thereof.

9. The sheath type disposable safety scalpel according to claim 1 wherein the blade protection locking notch includes a lock notch, which is a third concave notch, and a third blocking faces are provided at positions at a left, a right, and below, front face of the lock notch, and a cambered surface or slope is provided between the lock notch and the blade protection locking notch, the cambered surface or slope configured to make the locking head slide from the blade protection locking notch into the lock notch under a forward driving force.

10. The sheath type disposable safety scalpel according to claim 9 wherein an assembly inclined surface is provided under the lock notch and the assembly inclined surface is connected with or adjacent to the first unlocking inclined face on a rear end and the assembly inclined surface leads to an installation base direction of the blade on the front end, of the handle and when the sheath covers the handle, press the button and push the sheath backward, then the locking head slides from the assembly inclined surface to the blade protection locking notch.

* * * * *